(12) United States Patent
Cho et al.

(10) Patent No.: US 7,112,452 B2
(45) Date of Patent: Sep. 26, 2006

(54) METHOD AND SENSOR FOR DETECTING THE BINDING OF BIOMOLECULES BY SHEAR STRESS MEASUREMENT

(75) Inventors: Yoon-kyoung Cho, Gyeonggi-do (KR);
Sun-hee Kim, Gyeonggi-do (KR);
Kwang-wook Oh, Gyeonggi-do (KR);
Geun-bae Lim, Gyeonggi-do (KR);
Dae-sung Yoon, Gyeonggi-do (KR)

(73) Assignee: Samsung Electronics Co., Ltd., (KR)

( * ) Notice: Subject to any disclaimer, the term of this patent is extended or adjusted under 35 U.S.C. 154(b) by 703 days.

(21) Appl. No.: 10/278,691

(22) Filed: Oct. 23, 2002

(65) Prior Publication Data
US 2003/0077649 A1    Apr. 24, 2003

(30) Foreign Application Priority Data
Oct. 23, 2001    (KR) .............................. 2001-65484

(51) Int. Cl.
*G01N 33/543* (2006.01)
(52) U.S. Cl. .................. 436/518; 422/68.1; 422/82.01; 435/6; 435/7.2; 435/287.1; 435/287.2; 436/524; 436/527; 436/149; 436/150; 436/151; 436/806; 310/311; 310/312; 310/313 R
(58) Field of Classification Search ..................... None
See application file for complete search history.

(56) References Cited

U.S. PATENT DOCUMENTS 5,372,930 A    12/1994 Colton et al. .................. 435/6
6,033,913 A    3/2000 Morozov et al. .............. 436/86
6,043,031 A    3/2000 Koster et al. ................... 435/6
6,090,933 A    7/2000 Kayyem et al. ........... 536/25.3
6,096,273 A    8/2000 Kayyem et al. ........... 422/68.1
6,141,096 A    10/2000 Stern et al. .................. 356/318

FOREIGN PATENT DOCUMENTS

| EP | 0962759 A1 | 12/1999 |
| EP | 0 962 759 B1 | 8/2003 |
| WO | WO 01/23892 A1 | 4/2001 |

OTHER PUBLICATIONS

Adam B. Steel et al.; Electrochemical Quantitation of DNA Immobilized on Gold; Anal. Chem. 1998, 70, 4670-4677.

Daniel P. Little et al.; MALDI on a Chip: Analysis of Arrays of Low-Femtomole to Subfemtomole Quantities of Synthetic Oligonucleotides and DNA Diagnostic Products Dispensed by a Piezoelectric Pipet; Anal. Chem. 1997, 69, 4540-4546.

(Continued)

*Primary Examiner*—Christopher L. Chin
(74) *Attorney, Agent, or Firm*—Cantor Colburn LLP

(57) ABSTRACT

A method and sensor are provided for detecting the binding of a probe and a target biomolecule by measuring a difference in the shear stress on the surface of the sensor before and after hybridization of the target molecule to the probe, such as nucleic acids or proteins. The shear stress may be measured sensitively and conveniently as an electrical signal without additional fluorescent labeling and without use of expensive additional devices.

18 Claims, 6 Drawing Sheets

OTHER PUBLICATIONS

Yoshio Okahata et al.; Kinetic Measurements of DNA Hybridization of an Oligonucleotide-Immobilized 27-MHz Quartz Crystal Microbalance; Anal. Chem. 1998; 70: 1288-1296.

Mary E. Napier et al.; Probing Biomolecule Recognition with Electron Transfer: Electrochemical Sensors for DNA Hybridization; Bioconjugate Chem. 1997; 8; 906-913.

Koji Hashimoto et al.; Novel DNA sensor for electrochemical gene detection; Analytica Chimica Acta, 286 (1994) 219-224.

Guanghua Wu et al.; Origin of nanomechanical cantilever motion generated from biomolecular interactions; Proc. Natl. Acad. Sci.; Feb. 13, 2001; vol. 98; No. 4; pp. 1560-1564.

Steve Granick; Motions and Relaxations of Confined Liquids; Science; 1991; vol. 253; pp. 1374-1379.

Shana O. Kelley et al.; Photoinduced Electron Transfer in Ethidium-Modified DNA Duplexes: Dependence on Distance and Base Stacking; J. Am. Chem. Soc. 1997; 119, 9861-9870.

Claire E. Jordan et al.; Surface Plasmon Resonance Imaging Measurements of DNA Hybridization Adsorption and Streptavidin/DNA Multilayer Formation at Chemically Modified Gold Surfaces; Anal. Chem. 1997, 69, 4939-4947.

S. R. Sheth et al.; Interactions of Poly(ethylene oxide) Brushes with Chemically Selective Surfaces; J. Phys. Chem. B, 2000, 104, 7652-7662.

J. Fritz et al.; Translating Biomolecular Recognition into Nanomechanics; Science; Apr. 14, 2000; vol. 288; pp. 316-318.

"The surface force apparatus—a tool for probing molecular protein interactions"; NATURE. vol. 376; Aug. 17, 1995 Author: Deborah Leckband.

XP000219383; "Design of an Apparatus to Measure the Shear Response of Ultrathin Liquid Films"; 8127 Review of Scientific Instruments; 62(1991) Feb. No. 2, New York, US; Authors: James Peachey, John Van Alsten and Steve Granick; American Institute of Physics; pp. 463-473.

XP000525968; "The Surface Force Apparatus—A Tool for Probing Molecular Protein Interactions"; (PCT.195) 37 Natue; 376(1995) Aug. 17, No. 6541, London GB; Author: Deborah Leckband; pp. 671-618.

European Search Report of EP 02 02 3725, date of completion of the search Sep. 30, 2004.

METHOD AND SENSOR FOR DETECTING THE BINDING OF BIOMOLECULES BY SHEAR STRESS MEASUREMENT

BACKGROUND OF THE INVENTION

This application claims the priority of Korean Patent Application No. 2001-65484, filed Oct. 23, 2001, in the Korean Intellectual Property Office, the disclosure of which is incorporated herein in its entirety by reference.

1. Field of the Invention

The present invention relates to a method for detecting the binding of biomolecules, and more particularly, to a method and sensor for detecting the binding of probes and target biomolecules on a bio-chip by measuring the shear stress on a sensor substrate, to which the biomolecules are bound, before and after binding of the target molecules to the probes.

2. Description of the Related Art

Bio-chips, which are constructed by attaching a number of DNA or protein probes having a complementary sequence that can bind to target molecules of interest on a substrate at a high density, are used for analyzing a gene expression pattern, deficiency, protein distribution, or reaction pattern in the target sample. Bio-chips can be classified into micro-array chips with probes immobilized on a solid surface and labs-on-a-chip with probes immobilized on micro-channels according to the way probes are attached. Bio-chips also can be classified into DNA-chips, protein-chips, etc., according to the kind of the probes. Those bio-chips need a system for detecting the binding of biomolecules in a sample to the probes immobilized on a substrate in order to identify whether a target biomolecule of interest exists in the sample.

Most currently available DNA chips for gene array fluorescently detect target molecules in a sample. U.S. Pat. No. 6,141,096 discloses such an optical biomolecular detection method involving labeling sample DNAs with fluorescent dye, reacting the sample DNAs with probes immobilized on a chip, and detecting the samples DNAs which are fluorescently labeled and bound to the surface of the chip using a confocal microscope or CCD camera. However, it is difficult to apply the optical detection method to micro-sized chips.

U.S. Pat. Nos. 6,096,273 and 6,090,933 disclose electrochemical methods for detecting DNA hybridization using metallic compounds that are susceptible to oxidation and reduction. The metallic compounds form metal-DNA complexes through hybridization, and the metal-DNA complexes are electrochemically detected (Anal. Chem., Vol. 70, pp. 4670–4677, 1998; J. Am. Chem. Soc., Vol. 119, pp. 9861–9870, 1997; Analytica Chimica Acta, Vol. 286, pp. 219–224, 1994; Bioconjugate Chem., Vol. 8, pp. 906–913, 1997). However, the electrochemical method also inconveniently needs an additional labeling process.

Further, assay methods using no labels such as fluorescent dye have been developed. For example, a method for detecting the binding of biomolecules by measuring a difference in mass before and after binding using a quartz crystal microbalance is disclosed in Anal. Chem., Vol. 70, pp. 1288–1296, 1998. Assay methods involving matrix assisted laser desorption/ionization (MALDI) mass spectrometry are disclosed in Anal. Chem., Vol. 69, pp. 4540–4546, 1997 and U.S. Pat. No. 6,043,031.

Micromechanical methods capable of detecting even a single base mismatch are disclosed in Science, Vol. 288, pp. 316–318, 2000 and Proc. Natl. Acad. Sci. USA, 98, 1560, 2001, which use a microfabricated cantilever as a mechanical sensor for detecting the molecular binding force before and after binding of DNA probes and target molecules. However, the method needs an expensive separate laser device in order to precisely measure the deflection of cantilever beams.

Therefore, there is a need to develop a method for sensitively and efficiently detecting the binding of biomolecules directly as an electrical signal without using expensive additional devices, such as a laser device.

SUMMARY OF THE INVENTION

Accordingly, the present invention provides a method for detecting the binding of probes and target biomolecules as an electrical signal without additional labeling.

The present invention also provides a shear stress sensor used in the above method for detecting the binding of probes and target molecules.

In one aspect, the present invention provides a method for detecting the binding of probe biomolecules and target biomolecules, comprising: (a) immobilizing probe biomolecules on a surface of a sensor substrate; (b) loading a sample containing target biomolecules onto a sample plate arranged parallel to and facing the surface of the sensor substrate; (c) adjusting the distance between the sensor substrate and the sample plate to correspond to the size of the biomolecules; (d) reacting the probe biomolecules on the sensor substrate with the target biomolecules of the sample; and (e) measuring a change in the shear stress on the surface of the sensor substrate before and after the reaction in step (d).

In the method according to the present invention, the change in the shear stress is measured from a phase shift and a force change in the vibrations of the sensor substrate. Briefly, a general shear stress measuring method (J. Van Alsten, and S. Granick, Rev. Sci. Inst, 62, 463, 1991) involves oscillating signal input vibrating units in a sinusoidal mode and measuring a phase shift and a force change in signal output vibrating units from the input and output vibration measurements. Such a phase shift and force change is greatly affected by the viscosity or molecular structure of substances immobilized on the surface of the sensor substrate. Based on this, the binding of the probe biomolecules and the target molecules can be detected in the present invention.

In the method according to the present invention, the distance between the sensor substrate and the sample plate is adjusted to correspond to the known size of the biomolecules that are supposed to bind to the sensor substrate, and preferably, to correspond to the size of the biomolecules actually bound to the sensor substrate by measuring a normal force in the biomolecules bound to the sensor substrate while reducing the distance between the sensor substrate and the sample plate.

In the method according to the present invention, available probe and target biomolecules include DNA oligomers, nucleic acids such as c-DNA, proteins such as antigens and antibodies, cofactors, oligosaccharides, and cells. The probe molecules need to be able to selectively bind to the target molecules of interest.

In another aspect, the present invention provides a shear stress sensor comprising: a signal input unit which generates vibrations; a signal output unit which retards the vibrations of the signal input unit; a sensor substrate which bridges the signal input unit and the signal output unit; a sample plate arranged parallel to and facing a surface of the sensor substrate; a unit which adjusts the distance between the sensor substrate and the sample plate; and a signal detector unit which measures a phase shift and a force change from the vibrations of the signal input and output units.

In the sensor according to the present invention, any mechanism capable of inducing the signal input and output units to periodically vibrate and capable of measuring the amounts of vibrations can be applied to the signal input and output units. It is preferable that the vibrations of the signal input and output units be induced by a piezoelectric voltage, electrostatic capacitance, an electromagnetic current, or thermal expansion.

In the sensor according to the present invention, a plurality of sensor units, each of which includes the signal input unit, the signal output unit, and the sensor substrate, can be arrayed. This array structure of the shear stress sensor can be effectively used for bio-chips including a number of probes immobilized on the chip.

In the sensor according to the present invention, the unit which adjusts the distance between the sensor substrate and the sample plate can be any apparatus capable of adjusting the distance between the sensor substrate, on which probes molecules are immobilized, and the sample plate and, preferably, comprises a capacitance measuring apparatus. It is important to precisely adjust the distance between the sensor substrate and the sample plate since the shear stress of the biomolecules bound to the sensor substrate depends on the distance between the sensor substrate and the sample plate. The distance adjusting unit adjusts the distance between the sensor substrate and the sample plate to correspond to the size of the biomolecules bound to the sensor substrate.

In the sensor according to the present invention, the signal detector unit can be implemented with any apparatus capable of measuring a phase shift and force change from the vibrations of the signal input and output units or capable of measuring the elastic shear modulus or viscous shear modulus of the sensor substrate. For example, the signal detector unit can be implemented with a lock-in amplifier.

BRIEF DESCRIPTION OF THE DRAWINGS

The above features and advantages of the present invention will become more apparent by describing in detail exemplary embodiments thereof with reference to the attached drawings in which.

DETAILED DESCRIPTION OF THE INVENTION

Hereinafter, embodiments of the present invention will be described in detail with reference to the appended drawings.

Figure 1:
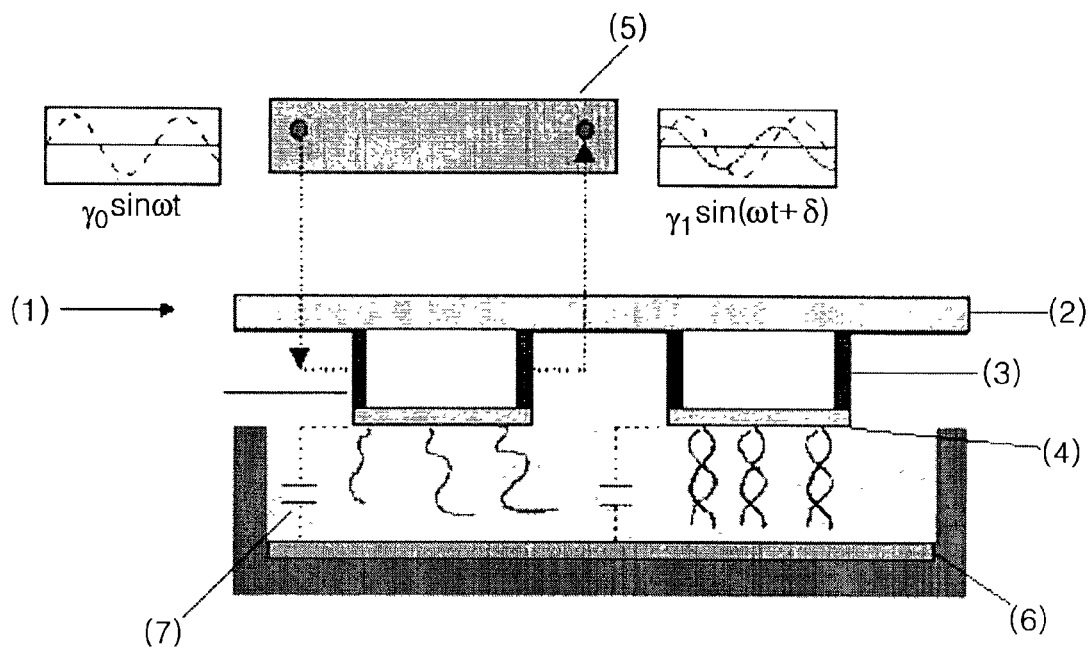
FIG. 1 is a schematic view of a shear stress sensor using piezoelectric vibrating plates according to an embodiment of the present invention.

FIG. 1 is a schematic view of a shear stress sensor using piezoelectric vibrating plates according to an embodiment of the present invention. As shown in FIG. 1, a shear stress sensor 1 includes a support substrate 2, two vibrating plates 3 and 3' attached to the support substrate, and a sensor substrate 4 bridging the two vibrating plates 3 and 3'. One vibrating plate 3 is used as a signal input unit, and the other vibrating plate 3' is used as a signal output unit. The vibrating plates 3 and 3', for example, piezoelectric bimorphs, are vibrated by piezoelectric force and the vibration motion is detected by a signal detector 5 which measures a phase shift and force change in a sinusoidal signal output from the two vibrating plates 3 and 3'. DNA or protein probes that specifically bind to a target sample are immobilized on a surface of the sensor substrate 4. A sample plate 6 on which the target sample is to be loaded and the sensor substrate 4 are arranged parallel to each other. The distance between the sensor substrate 4 and the sample plate 6 can be adjusted by vertically moving the support substrate 2 or the sample plate 6 using a mechanical apparatus (not shown), for example, a capacitance measuring apparatus 7.

Figure 2A:
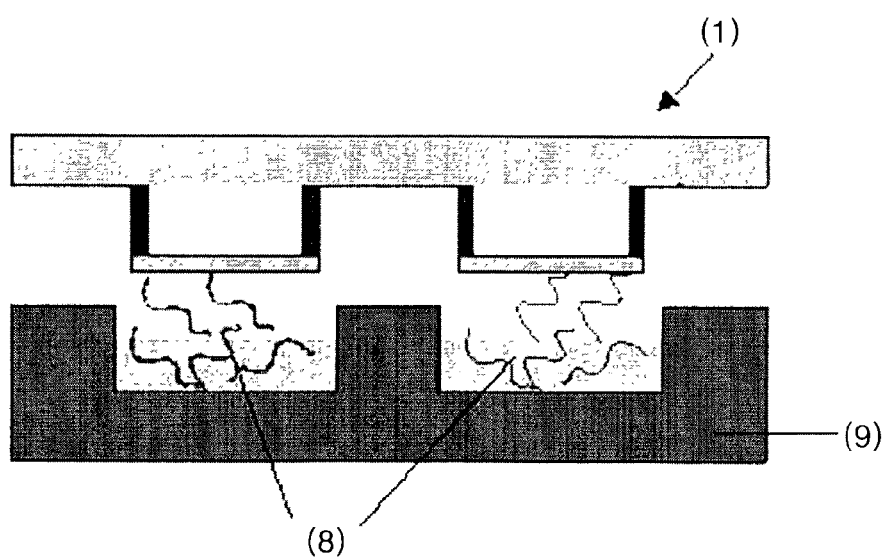
FIG. 2A illustrates a method for immobilizing various kinds of probes on a shear stress sensor array according to the present invention.
Figure 2B:
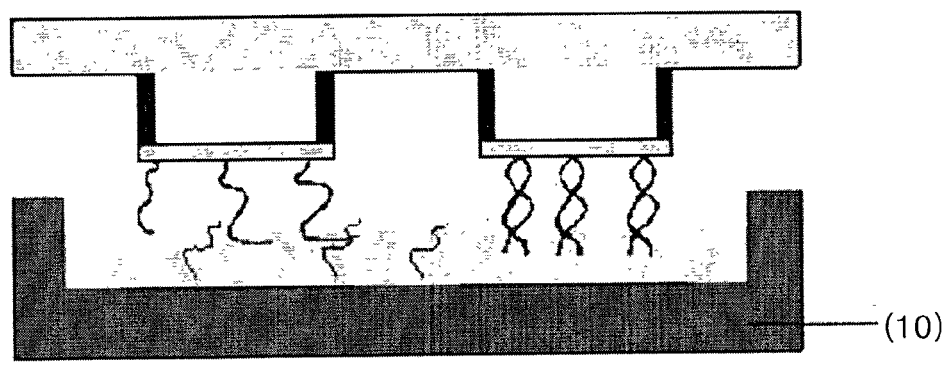
FIG. 2B illustrates a method for hybridizing the probes of FIG. 2A to a target sample of interest.

FIG. 2A illustrates a method for immobilizing various kinds of probes on a shear stress sensor array according to the present invention, and FIG. 2B illustrates a method for hybridizing the probes of FIG. 2A to a target sample of interest. In FIG. 2A, the various kinds of probes 8 are immobilized on the sensor array 1 having the vibrating plates 3 and 3' by putting the array sensor 1 into a multi-well probe container 9. In FIG. 2B, the array sensor 1 with the immobilized probes are put into a single-well container 10 containing the target sample to hybridize the target sample to the immobilized probes. A sample plate (not shown) is located on the bottom of the signal-well container 10. After hybridization, the array sensor 1 is washed, and the shear stress of the hybridized biomolecules is measured in a buffer solution.

Figure 3:
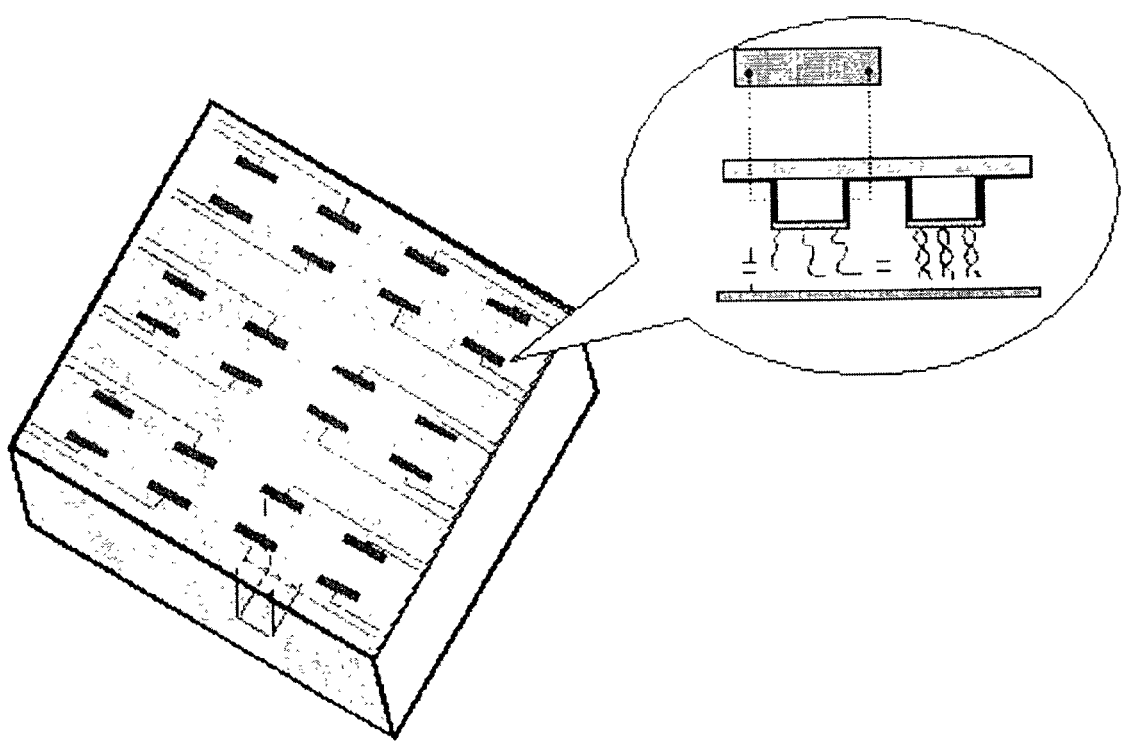
FIG. 3 is a schematic view of a sensor array according to the present invention including a number of sensor units each of which has the structure of the sensor of FIG. 1.

FIG. 3 is a schematic view of a sensor array according to the present invention including a number of sensor units each of which has the structure of the sensor of FIG. 1. In FIG. 3, a pair of bars corresponds to one sensor unit including the signal input unit 3, the signal output unit 3', and the sensor substrate bridging the signal input and output units 3 and 3', as shown in FIG. 1.

Figure 4:
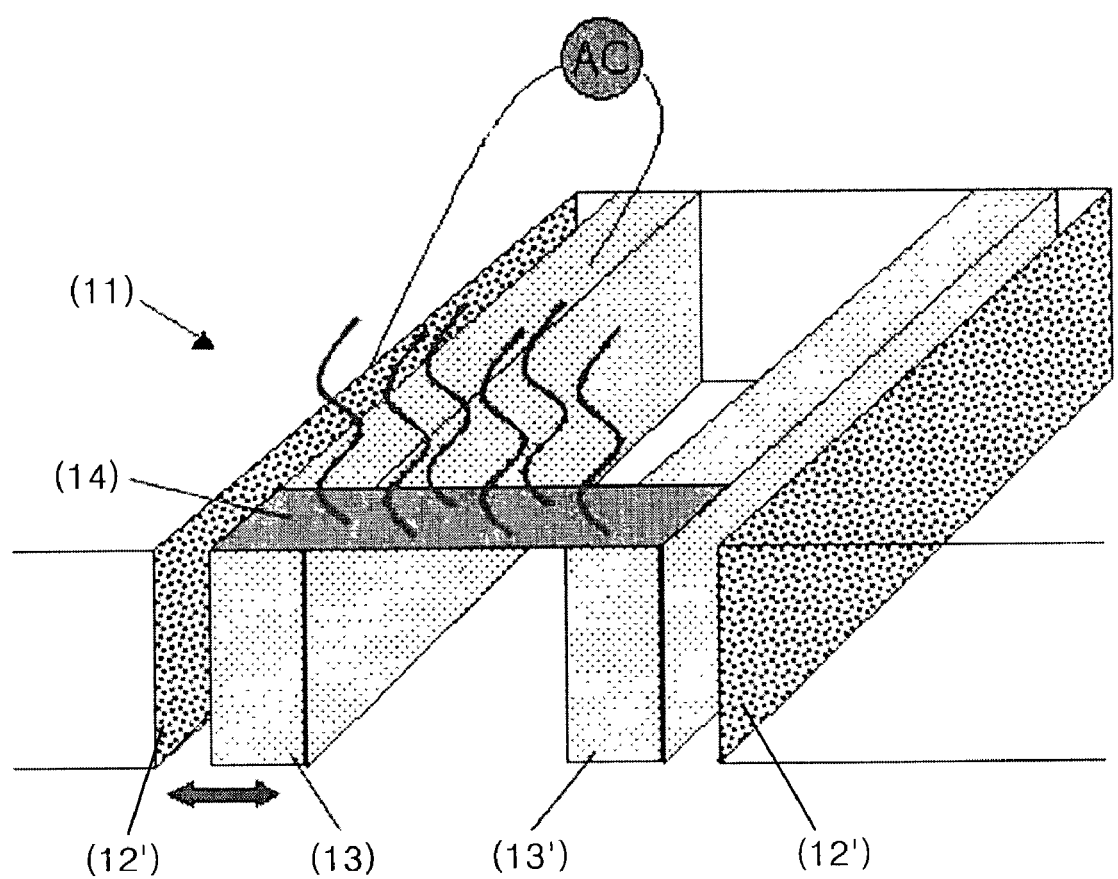
FIG. 4 is a schematic view of a shear stress sensor array using electrostatic vibrating plates according to another embodiment of the present invention.

FIG. 4 is a schematic view of a shear stress sensor array using electrostatic vibrating plates according to another embodiment of the present invention. In FIG. 4, a shear stress sensor 11 includes two vibrating plates 13 and 13', plates 12 and 12' fixed adjacent to the respective vibrating plates 13 and 13', and a sensor substrate 14 bridging the vibrating plates 13 and 13'. The vibrating plates 13 and 13' of the shear stress sensor 11 oscillate by electrostatic force rather than piezoelectric force in the shear stress sensor 1 of FIG. 1. The vibrations of the vibrating plates 13 and 13' are detected by measuring a difference in capacitance between the vibrating plates 13 and 13' and the respective plates 12 and 12'.

The principles of measuring shear stress in a sensor array according to the present invention will be described briefly (J. Van Alsten, and S. Granick, Rev. Sci. Inst, 62, 463, 1991). While oscillating one vibrating plate acting as a signal input unit in a sinusoidal mode, the vibrations of the other vibrating plate acting as the signal output unit are electrically measured, and an intensity deflection (force change) and phase shift in the input and output measurements is read. The intensity deflection and phase shift is greatly affected by the viscosity or molecular structure of substances immobilized on the surface of the sensor array. The shear stress of elastic solids is proportional to strain according to the Hook's law, while that of liquids is proportional to shear rate according to the Newton's law. The shear stress of viscoelastic liquids is expressed by elastic shear modulus (or storage modulus) as an elastic component and viscous shear modulus (or loss modulus) as a viscous component or dissipative component. The elastic component and deformation are in phase, and the viscous component is proportional to shear rate, i.e., deformation rate.

The local viscosity as a function of flow distance of molecules on a surface cannot be measured accurately. However, the effective viscosity as a flow resistance can be measured from the viscosity component of the shear stress and is defined as viscous stress/effective shear rate. The effective shear rate corresponds to the maximum shear amplitude or thickness of molecular layers.

The present invention will be described in greater detail with reference to the following examples. The following examples are for illustrative purposes and are not intended to limit the scope of the invention.

EXAMPLE 1

Immobilization of Thiol-substituted DNA Oligomer Probes

To measure the difference in shear stress before and after hybridization, a surface forces apparatus which is modified to measure lateral (shear) forces (Granick, S. *Science,* 1991, 253, 1374) was used. According to a general surface force measuring method, muscovite mica was cleaved into step-free, smooth substrates in an automated manner. Silver (Ag) was deposited on one cleaved surface of each of the mica substrates to a thickness of 660 Å by sputtering, and a lens having a radius of curvature (R) of ~2 cm was attached to the outer surface of the mica substrate having the Ag-coated inner surface using glue.

Thiol-substituted DNA oligomer probes were immobilized on the inner Ag surface of one of the mica substrate. The gap between the two mica substrates was measured by multiple beam interferometry (Journal of Colloid and Interface Science, 1993, 44(2), 259, and *J. Phys. Chem. B.,* 2000, 104, 7652). In a general experiment for measuring surface forces, two mica substrates are disposed such that their Ag surfaces face outward and a liquid sample is applied between the inner surfaces of the mica substrates. However, according to the present invention, the mica substrates were assembled such that the Ag surface of one mica substrate faces the non-Ag surface (or bare mica surface) of the other mica substrate, so that self-assembled monolayers of the DNA probes that will bind to target molecules are immobilized on the inner Ag surface of one mica substrate.

When the distance between the two mica substrates was 300 Å, the substrates jumped into flat contact by strong van der Waals interaction, indicating that the opposite Ag surface and non-Ag surface of the mica substrates are very clean. Constructive interference wavelengths measured at several contact points between the Ag surface and non-Ag surface remained almost constant within the range of 2–4 Å. Although the roughness of the Ag surface Ag layer was estimated to be 15–20 Å, the distance between the two surfaces could be exactly measured. The refractive index of a DNA probe solution, which is required for calculating the thickness of the self-assembled monolayers, was supposed to be 1.46 (Jordan, C. E.; Frutos, A. G.; Thiel, A. T.; Corn, R. M. *Anal. Chem.* 1997, 69, 4939).

An oligonucleotide corresponding to a region of the iduronate-2-sulphate (IDS) exon gene causing Hunter's syndrome was used for the oligomer probes; the sequence of the oligonucleotide was SH-$C_6$-5'-GTT CTT CTC ATC ATC-3' (SEQ ID NO:1). The oligomer probes were purchased from Research Genetics (Huntsville, Ala.), and their 5'-ends were substituted with alkane thiol spacers each having a molecular weight of 4651 g/mol. The inner Ag surface of the mica substrate was soaked in a 1-mM solution of thiol-substituted single-stranded DNA (ss-DNA) probes in 1M $NaH_2PO_4$ (pH 4.0) for 3 hours to adsorb the ss-DNA probes onto the inner Ag surface. Next, the inner Ag surface was washed with a buffer solution and then deionized water, and dried with nitrogen gas. The physisorbed DNA probes were removed from the inner Ag surface, and the inner Ag surface was soaked in 1 mM mercaptohexanol and HS—$(CH_2)_6$OH for 10 minutes in order for the ss-DNA probes to extend toward the bare mica surface of the opposite mica substrate, washed with deionized water, and dried with nitrogen gas.

EXAMPLE 2

Probe Hybridization to Complementary Sequence

For hybridization, the ss-DNA probes were reacted with a 1.5-mM solution of ss-DNA oligomers having a complementary sequence (, i.e., 3'-CAA GAA GAG TAG TAG-5') (SEQ ID NO: 2) to the probes, in TE-1M NaCl buffer (10 mM Tris-HCl, 1 mM EDTA, 1 M NaCl) at 38° C. and pH 7.6 for 2 hours, washed with 38° C.-TE-1M NaCl buffer and then deionized water, and dried with nitrogen gas.

EXAMPLE 3

Normal Force Measurement

Normal force was measured using a modified surface forces apparatus, which operates according to the principles of the sensor of FIG. 1 (S. Granick, Science, 253, 1374, 1991, J. Peachey, J. Van Alsten, and S. Granick, Rev. Sci. Inst, 62, 463, 1991). After the adsorption of the thiol-substituted oligomer probes on the inner Ag surface of the mica substrate as self-assembled monolayers, the compressive force of the self-assembled probe monolayers before and after hybridization of the target sample to the same were measured.

One droplet of 1M NaCl solution was dispensed between the two opposite inner surfaces of the mica substrates, while the ss-DNA probes were immobilized on the Ag surface of one mica substrate or were hybridized with the target sample. At this time, the Ag surface of one mica substrate on which the thiol-substituted DNA probes were immobilized or which includes the thiol-substituted DNA probes hybridized with the target sample was placed above and facing the bare mica surface.

As a result of an experiment conducted for comparison, the DNA probes were found not to adsorb onto the bare mica surface, which is negatively charged in water. Therefore, the thiol-substituted DNA oligomer probes have one end tethered to the Ag surface and rarely nonspecifically adsorb on the opposite bare mica surface.

In the state where the Ag surface and the bare mica surface were spaced longer than 1 mm apart, one droplet of 1M NaCl solution was applied between the two opposite surfaces, and the thickness of the DNA monolayer between the two opposite surfaces was measured by multiple beam interferometry while narrowing the gap between the two surfaces by applying a force to springs which support the base of the mica substrate with the bare mica surface. The distance by which the two mica substrates were actually moved was compared with the distance by which the two mica sheets are nominally supposed to be moved, using the applied force and the elastic constant of the springs. As a result, the force-distance curve in the upper graph of FIG. 5 was obtained.

Figure 5:
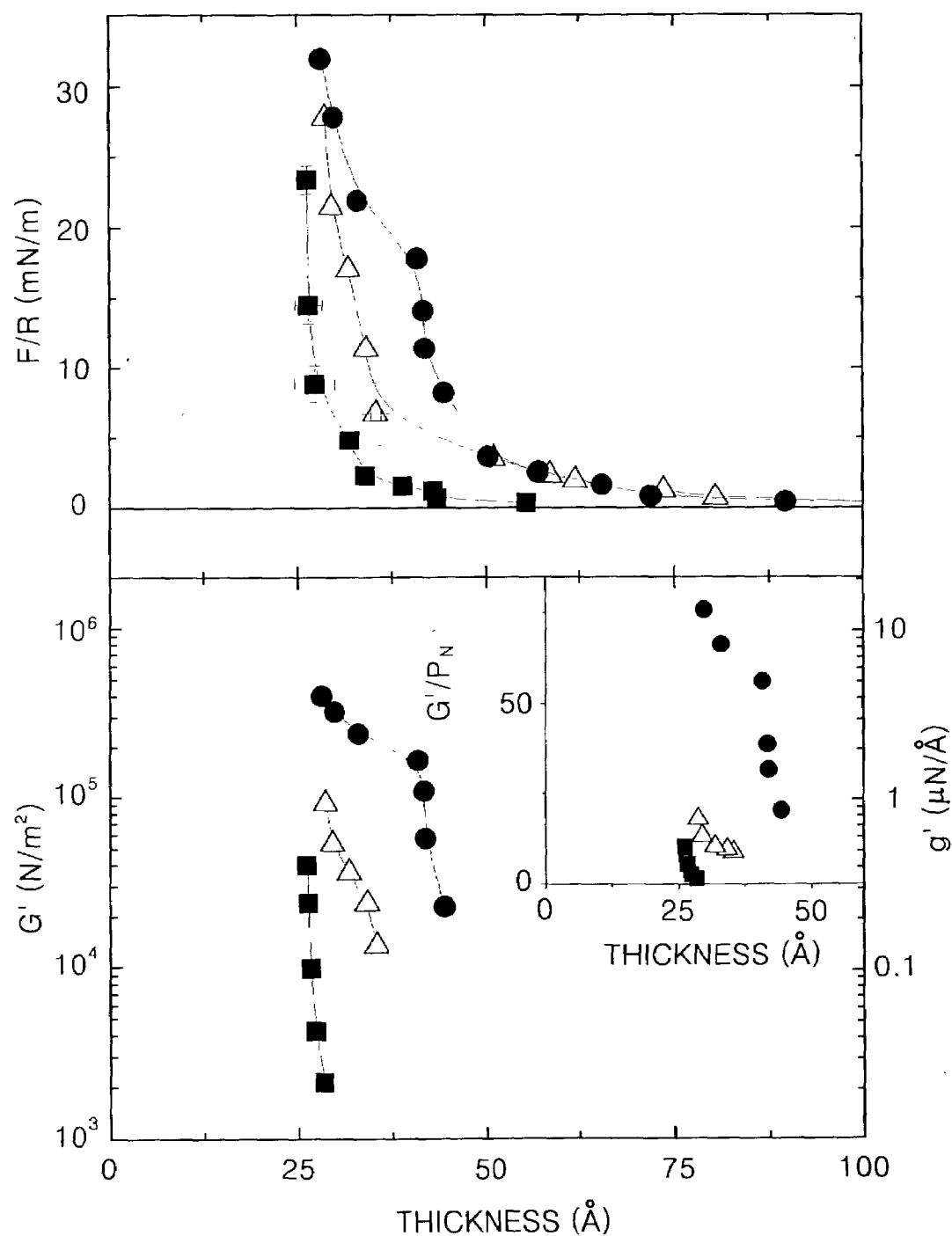
FIG. 5 illustrates the compress force (upper graph) and the shear stress (lower graph) of DNA monolayers, comparatively before and after hybridization, which were measured using a modified surface forces apparatus operating according to the principles of the sensor of FIG. 1.

FIG. 5 shows the data measured using a modified surface forces apparatus operating according to the principles of the sensor of FIG. 1 (S. Granick, Science, 253, 1374, 1991, J. Peachey, J. Van Alsten, and S. Granick, Rev. Sci. Inst, 62, 463, 1991). In particular, the compressive force (upper graph) and shear stress (lower graph) of the self-assembled monolayers of thiol-substituted oligomer probes immobilized on the Ag surface before and after hybridization to a complementary sequence were measured. In FIG. 5, the rectangular symbol (■) is for the ss-DNA probes in 0.1M NaCl, the triangular symbol (∆) is for the ss-DNA probes in 1.0 M NaCl after an addition of excess mercaptohexanol, and the circular symbol (●) is for the double-stranded DNA (ds-DNA) probes in 1.0 M NaCl after hybridization. In the upper graph of FIG. 5, Y-axis represents the compressive force (F/R) normalized with respect to the radius of curvature of the lens, and X-axis represents the thickness of the molecular monolayer between the Ag surface and the bare mica surface. In the lower graph of FIG. 5, Y-axis on the left represents the shear stress, i.e., the effective elastic shear modulus (G'), normalized with respect to effective contact area, Y-axis on the right represents the elastic shear constant (g') which is not normalized with respect to effective contact area, and X-axis represents the thickness of the molecular monolayer between the Ag surface and the bare mica surface. The shear stress was plotted on a semi-logarithmic scale. In the insect of FIG. 5, a ratio of the normal force ($P_N$) to the sheer stress G' is shown. The shear stress was measured by applying a frequency of 1.3 Hz, and the effective contact area was calculated using Langbein approximation ($A_{eff}$~2π RD).

For reference, the contour length of the ss-DNA 15-mer and the ds-DNA in the experiment was estimated to be 77 Å and 63 Å, respectively. As is indicated by the rectangular symbol (■) in the upper graph of FIG. 5, when only thiol-substituted ss-DNA probes are immobilized on the Ag surface in 1.0M NaCl, without the post-treatment with mercaptohexanol, a repulsive force was generated when the thickness of the probe monolayer reached about 43±2 Å, and the hard wall thickness of the probe monolayer at which no compression occurs any longer was 26±2 Å.

When the Ag surface of the mica sheet having the immobilized ss-DNA probes was treated with mercaptohexanol, as indicated by the triangular symbol (∆), since the ss-DNA probes extended toward the opposite bare mica surface, the thickness of the probe monolayer at which a repulsive force in the probes is generated increased to about 80±2 Å, and the hard wall thickness increased to about 26±2 Å, which are both greater than those of the ss-DNA probe monolayer before treatment with mercaptohexanol.

After formation of the double-stranded DNA (ds-DNA) probes through hybridization, as indicated by the circular symbol (●), the repulsive force in the ds-DNA monolayer was generated at a thickness of about 72±2 Å and monotonically increased as the ds-DNA probe monolayer was compressed to a thickness of 41±2 Å. Also, an abrupt reduction in the thickness of the ds-DNA monolayer from 41±2 Å to 30±2 Å occurred. This is considered due to the tilting of the individual ds-DNA oligomers at an angle caused by an excess normal pressure applied to the rigid ds-DNA monolayer. Therefore, the actual thickness of the ds-DNA monolayer is estimated to be in the range of from 41±2 Å to 30±2 Å.

As described above, whether or not hybridization occurs in the silver surface of the mica substrate can be determined by measuring changes in the repulsive force of the DNA probes immobilized on the silver surface while approaching the silver surface to the opposite bare mica surface of the other mica substrate. In other words, the thickness of ss-DNA and ds-DNA oligomer monolayers or changes in the force of the monolayers can be determined by accurately measuring such normal force exerted in the monolayers. However, it is difficult to accurately measure such normal force, and the difference in normal force between single- and double-stranded oligomers is very small compared with shear stress.

EXAMPLE 4

Shear Stress Measurement

In this example, shear stress was measured to detect DNA hybridization, instead of the normal force in Example 3. To detect DNA hybridization, the lateral stiffness of DNA molecules was measured using a shear stress measuring apparatus, for example, a lock-in amplifier as shown in FIG. 1. The shear amplitude was smaller than 2 Å to carry out the experiment in a linear regime not to disturb the system operation.

The vibrating plate 3 acting as the signal input unit was excited by applying various frequencies in a sinusoidal mode, and the vibrations of the other vibrating plate 3' acting as the signal output unit were measured to read the in-phase modulus (elastic force) or the out-of-phase modulus (viscous force) from the input and output measurements. The measured elastic force is shown in the lower graph of FIG. 5. As is apparent from FIG. 5, the elastic force greatly increased after hybridization. The reason for this is considered to be due to the stiffness of the hybridized ds-DNA oligomers greater than that of ss-DNA probes.

Referring to the inset of FIG. 5, as is apparent from the normalization of the shear stress G' with respect to the normal pressure PN, the shear stress G' is greater than the normal pressure $P_N$. Accordingly, shear force is considered to be a more sensitive measure than normal force for hybridization detection.

Figure 6:
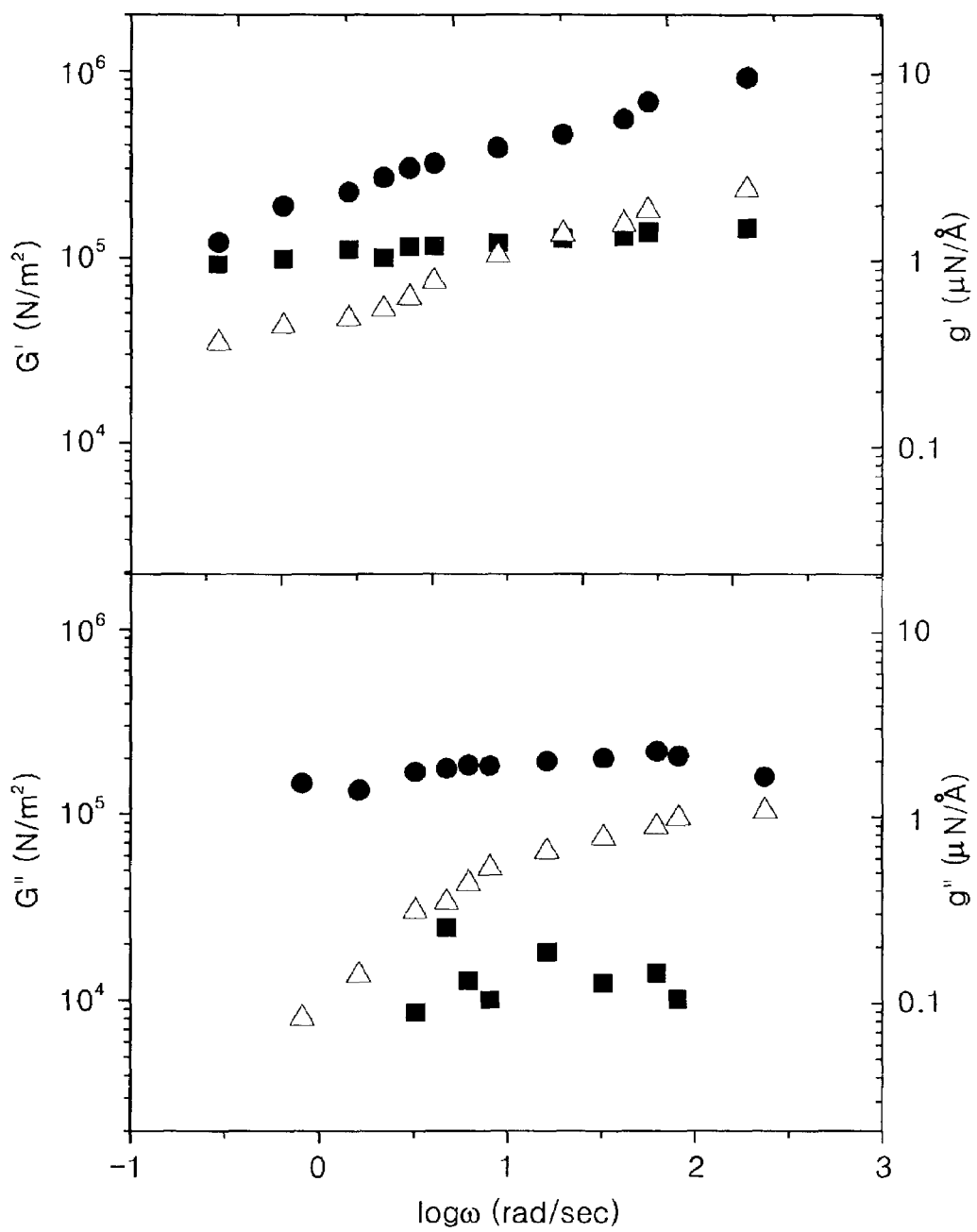
FIG. 6 comparatively illustrates the elastic shear modulus (upper graph) and the viscous shear modulus (lower graph) of ss- and ds-DNA monolayers, which were measured by applying shear stresses of various frequencies while the distance between a sensor substrate and a sample plate was fixed to 31±2 Å.

The elastic force in the lower graph of FIG. 5 was measured by applying a constant shear amplitude and shear frequency while reducing the distance between the two mica substrates. FIG. 6 comparatively illustrates the elastic shear modulus (upper graph) and the viscous shear modulus (lower graph) of ss- and ds-DNA monolayers, which were measured by applying shear stresses of various frequencies to the mica substrate, to which DNA molecules were bound, while the distance between the sensor substrate 4 and the sample plate 6 was fixed to 31±2 Å, which corresponds to the size of the DNA molecules and was determined based on the experimental results from FIG. 5. In FIG. 6, the same reference symbols as in FIG. 5 denote the same DNA oligomers as in FIG. 5. In FIG. 6, the Y-axes on the left of the upper and lower graphs represent the effective elastic shear modulus G' and the effective viscous shear modulus G", respectively, which were normalized with respect to effective contact area using Langbein approximation. The Y-axes on the right of the upper and lower graphs represent the elastic shear constant g' and the viscous shear constant g", respectively, which were not normalized with respect to effective contact area. The X-axis of the upper and lower graphs represents the radian shear frequency. As shown in FIG. 6, the elastic modulus and viscous modulus of the ds-DNA oligomers after hybridization were greater than those of the ss-DNA primers before hybridization by an order of magnitude. Therefore, DNA hybridization can be effectively detected by measuring those shear stresses, which is the essential feature of the present invention.

Figure 7:
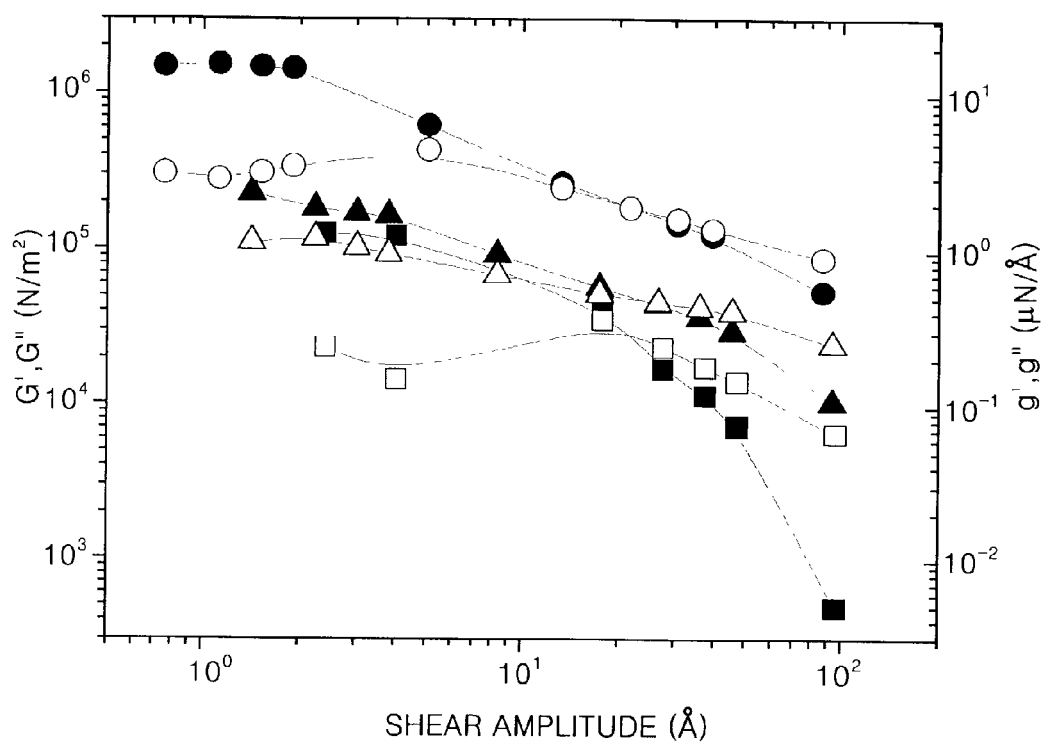
FIG. 7 comparatively illustrates the elastic shear modulus and viscous shear modulus of ss- and ds-DNA oligomers with respect to shear amplitude variations, which were measured while the distance between the sensor substrate and the sample plate was 31±2 Å.

FIG. 7 illustrates the elastic shear modulus and viscous shear modulus with respect to shear amplitude variations, comparatively in ss- and ds-DNA oligomers, which were measured while the distance between the sensor substrate 4 and the sample plate 6 was 31±2 Å. In FIG. 7, the rectangular symbols (■ and □) denote the elastic shear modulus and the viscous shear modulus, respectively, of the ss-DNA probes in 1.0M NaCl, the circular symbols (● and ○) denote the elastic shear modulus and the viscous shear modulus, respectively, of the ss-DNA probes in 1.0 M NaCl after an addition of excess mercaptohexanol, and the triangular symbols (▲ and △) denote the elastic shear modulus and the viscous shear modulus, respectively, of the ds-DNA oligomers after hybridization in 1.0 M NaCl. The elastic shear modulus and the viscous shear modulus were normalized with respect to effective contact area using the same method applied to obtain the results of FIG. 6. When the shear amplitude was increased beyond a limit, those shear moduli decreased. However, even when the shear stress of a sample is measured in a non-linear regime by increasing the shear amplitude to a level of tens of nanometers, the difference in the shear modulus between ss-DNA probes before hybridization and ds-DNA oligomers after hybridization is much greater than an order of magnitude.

Although in the above-described example a target sample having a perfectly matching sequence was used, the hybridization of a mutant sample, for example, having a single point mutation, to ss-DNA probes can be effectively detected.

As described above, in the method for detecting the binding of biomolecules, such as DNAs or proteins, according to the present invention, the binding of target molecules to probes on the sensor surface can be detected by measuring a difference in the shear stress of biomolecules bound to the sensor surface before and after hybridization. Unlike conventional fluorescent molecular detecting methods, the binding of biomolecules can be directly detected as an electrical signal without additional labeling. The method according to the present invention is more sensitive than conventional methods of measuring the deflection of cantilever beams and needs no expensive separate equipment, such as a laser device.

While the present invention has been particularly shown and described with reference to preferred embodiments thereof, it will be understood by those of ordinary skill in the art that various changes in form and details may be made therein without departing from the spirit and scope of the present invention as defined by the following claims.

What is claimed is:

1. A method for detecting a binding of a probe and a target biomolecule, comprising:

immobilizing the probe on a surface of a sensor substrate;

loading a sample containing the target biomolecule onto a sample plate arranged parallel to and facing the surface of the sensor substrate;

adjusting a distance between the sensor substrate and the sample plate to a size of the target biomolecule;

contacting the probe immobilized on the sensor substrate with the sample; and measuring a change in a shear stress on the surface of the sensor substrate to detect binding between the probe and target molecule by measuring shear stress before and after binding the probe and target biomolecule.

2. The method of claim 1, wherein the change in the shear stress is measured from a phase shift and a force change in a vibration of the sensor substrate.

3. The method of claim 1, wherein the adjusting the distance between the sensor substrate and the sample plate comprises measuring a normal force in the target biomolecule bound to the sensor substrate while reducing the distance between the sensor substrate and the sample plate.

4. The method of claim 1, wherein the target biomolecule comprises nucleic acids, proteins, cofactors, oligosaccharides, cells, or combinations of one or more of the foregoing molecules.

5. The method of claim 1, wherein the probe comprises nucleic acids, proteins, cofactors, oligosaccharides, cells, or combinations of one or more of the foregoing biomolecules.

6. The method of claim 1, wherein the probe comprises DNA and wherein the DNA comprises an alkane thiol spacer.

7. The method of claim 1, wherein the sensor substrate comprises mica.

8. The method of claim 7, wherein a first surface of the substrate comprises silver and a second surface of the substrate comprises a lens.

9. A shear stress sensor comprising:
a signal input unit which generates vibrations;
a signal output unit which retards the vibrations of the signal input unit;
a sensor substrate which bridges the signal input unit and the signal output unit, the sensor substrate comprising a probe;
a sample plate arranged parallel to and facing a surface of the sensor substrate;
an adjustment unit which adjusts a distance between the sensor substrate and the sample plate; and
a signal detector unit which measures a phase shift and a force change of the vibrations of the signal input and output units.

10. The sensor of claim 9, wherein the vibrations of the signal input and output units are induced by a piezoelectric voltage, electrostatic capacitance, an electromagnetic current, or thermal expansion.

11. The sensor of claim 9, wherein the sensor comprises an array of sensor units, each sensor unit comprising the signal input unit, the signal output unit, and the sensor substrate.

12. The sensor of claim 9, wherein the adjustment unit comprises a capacitance measuring apparatus.

13. The sensor of claim 9, wherein the probe comprises nucleic acids, proteins, cofactors, oligosaccharides, cells, or combinations of one or more of the foregoing biomolecules.

14. The sensor of claim 13, wherein wherein the probe comprises DNA and wherein the DNA comprises an alkane thiol spacer.

15. The sensor of claim 9, wherein the sensor substrate comprises mica.

16. The sensor of claim 15, wherein a first surface of the substrate comprises silver and a second surface of the substrate comprises a lens.

17. The sensor of claim 9, wherein the vibrations of the signal output and the signal input are induced by a piezoelectric voltage, an electrostatic capacitance, an electromagnetic current, or a thermal expansion.

18. The sensor of claim 9, wherein the sensor detector unit comprises a lock-in amplifier.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial
<220> FEATURE:
<223> OTHER INFORMATION: probe

<400> SEQUENCE: 1
gttcttctca tcatc                                                   15

<210> SEQ ID NO 2
<211> LENGTH: 15
<212> TYPE: DNA
<213> ORGANISM: Artificial
<220> FEATURE:
<223> OTHER INFORMATION: probe

<400> SEQUENCE: 2
caagaagagt agtag                                                   15
```